United States Patent [19]

Sung et al.

[11] Patent Number: 4,464,276

[45] Date of Patent: Aug. 7, 1984

[54] POLYOXYALKYLENE POLYAMINE TRIAZOLE COMPLEXES

[75] Inventors: Rodney L. Sung, Fishkill; Benjamin H. Zoleski, Beacon, both of N.Y.

[73] Assignee: Texaco Inc., White Plains, N.Y.

[21] Appl. No.: 492,313

[22] Filed: May 6, 1983

[51] Int. Cl.$^3$ .............................................. C10M 1/32
[52] U.S. Cl. .................................. 252/42.7; 252/50; 252/51.5 A; 252/390; 548/262; 548/269
[58] Field of Search ................... 252/42.7, 51.5 A, 50, 252/390; 548/262, 269

[56] References Cited

U.S. PATENT DOCUMENTS

| | | | |
|---|---|---|---|
| 4,144,180 | 3/1979 | Andress, Jr. | 252/50 |
| 4,197,210 | 4/1980 | Bridger | 252/50 |
| 4,278,553 | 7/1981 | Sung et al. | 252/51.5 R |
| 4,283,296 | 8/1981 | Nebzydoski et al. | 252/50 |

*Primary Examiner*—Jacqueline V. Howard
*Attorney, Agent, or Firm*—Robert A. Kulasen; Henry W. Archer; James J. O'Loughlin

[57] ABSTRACT

Novel polyoxyalkylene polyamine triazole or benzotriazole complexes for diesel oils used in medium speed diesel engines.

6 Claims, No Drawings

POLYOXYALKYLENE POLYAMINE TRIAZOLE COMPLEXES

BACKGROUND OF THE INVENTION

Field of the Invention

This invention relates to triazole derivatives and to fluid compositions containing same which are specially designed for use between two relatively moving surfaces for reducing friction therebetween and preserving the surfaces. More specifically, the invention discloses improved diesel lubricant compositions which impart superior oxidative stability and corrosion control to a medium speed, diesel engine oil containing a calcium carbonate overbased sulfurized calcium alkylphenolate.

Earlier formulations of this type contained various calcium sulfurized alkylphenolates which were designed to provide the finished oil with improved corrosion protection and/or oxidative stability. These phenolates included sulfurized $CO_2$-blown, double neutralized, normal calcium alkylphenolate, 2/1 overbased $Ca(OH)_2$ sulfurized calcium alkylphenolate and calcium reagent neutralized, sulfurized calcium alkylphenolate overbased by the hydrolysis of calcium reagent and blown with $CO_2$ for complete carbonation. These all were made by a process which employed a solvent recovery procedure which was expensive and wherein some of the byproducts that were trapped in the filter cake were hazardous to the environment upon disposal and did not meet EPA requirements. Accordingly, these detergents were replaced by calcium sulfurized phenolates made by a process utilizing lime as the source of calcium whereby the solvents system is eliminated and the disposed residue meets EPA regulations. These phenolates can be denominated 1/1 calcium carbonate overbased sulfurized calcium alkylphenolates and 2/1 overbased sulfurized calcium alkylphenolates containing calcium sulfonate. These detergents-dispersants do not however, provide the corrosion protection or oxidative stability medium speed diesel engine formulations that the calcium reagent produced phenolates provided. In order to attain the original performance with the lime prepared phenolates, it is necessary now to supplement the formulation with a corrosion and/or oxidation inhibitor.

DISCUSSION OF PRIOR DISCLOSURES

The prior art to which this invention relates evidences activity and includes coassigned U.S. Pat. Nos. 4,285,823, 4,320,016, 4,285,823, 4,169,799 and 4,172,269, the disclosures of which are incorporated herein by reference for their showing of diesel engine lubricant constituents.

Of these, U.S. Pat. No. 4,278,553 shows a corrosion inhibitor consisting of a benzotriazole, N-alkyl-1,3-propane diamine-formaldehyde condensation product. U.S. Pat. No. 4,285,823 shows a diesel lubricant composition comprising an oil corrosion inhibited by the incorporation of an N-substituted-5-amino-1H-tetrazole. While the above may be considered the most relevant prior art, there is no suggestion therein of the additives of this invention.

SUMMARY OF THE INVENTION

The invention provides novel polyoxyalkylene polyamine-triazole complexes having utility as diesel oil additives and which are represented generically by the following formula:

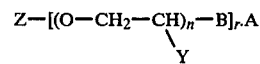

wherein Y is hydrogen or a (lower) alkyl radical having 1 to 5 carbon atoms; Z is a hydrocarbon radical having 2 to 10, and, preferably 4 carbon atoms, forming from 1 to 4 external ether linkages including lower alkyl, amino (lower) alkyl and ureido (lower) alkyl; n is a number from about 1 to about 15 and r is a number from 1 to 4; A is 5-aminotriazole or benzotriazole; B is $NH_2$ or ureido ($-NHCONH_2$) except that when Z is ureido (lower) alkyl and B is ureido, r can only be 1.

The invention also provides diesel lubricating oils containing at least one of the above additives together with an effective amount of a 1/1 calcium carbonate overbased sulfurized calcium alkylphenolate or of a 2/1 overbased sulfurized calcium alkylphenolate containing calcium sulfonate serving as a detergent inhibitor.

The lubricant compositions of the invention have a TBN or total base number defined as the quantity of acid expressed in terms of the equivalent number of milligrams of potassium hydroxide that is required to neutralize oil basic constituence present in one gram of a given sample as evaluated by ASTM method D664 of at least 5 owing to the presence therein of conventional additives and are thus capable of preventing corrosion by sludge formed by oxidative deterioration of oil at the high temperatures existing under normal conditions of engine use in proximity to the combustion chamber.

DISCLOSURE OF BEST MODE OF THE INVENTION

Preparation of the complexes used in a diesel lubricating composition according to this invention is relatively uncomplicated and can be economically conducted. The preparation entails mixing at room temperature with thorough agitation one part by weight of a triazole with from 40 to 160 parts by weight at least one polyoxyalkylene polyamine depicted by the formula:

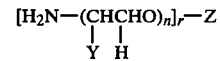

wherein Y, Z, n and r are as above. The most preferred polyoxyalkylene polyamines are the polyoxypropylenediamines wherein Y is a methyl radical, n is a number from 1 to 3, Z is a 2-amino propylene radical and r is 1. These polyoxyalkylene polyamines can be prepared by known methods as disclosed in U.S. Pat. Nos. 3,236,895 and 3,654,370 and are sold under the trademark name of "Jeffamines" by Jefferson Chemical Co., Austin, Tex. Some of these are sold as mixtures of amines.

The triazole reactant can be 5-aminotriazole or benzotriazole or derivatives thereof bearing noninterfering, inert substituents such as alkyl, nitro, cyano, trihaloalkyl and the like.

The effectiveness of the additives of the invention was tested by the Union Pacific Oxidation Test (UPOT). This test is used by railroads to judge the acceptability of an oil for use in their equipment. The test measures corrosion (50 mg. max. limit) and oxidative stability (20% max. viscosity increase at 100° F.) as well as other used oil parameters (pH-which is used by some railroads to judge the oil drain interval-below 5, drain; above 5, satisfactory; TBN can be used as a measure of alkaline retention). The test method involves bubbling 5 liters of oxygen per hour through 300 mls. of test oil composition at 285° F. in which there is immersed a 1×3×0.06 inch steel backed copper-lead test specimen cut from bearing stock. The viscosity of the test oil is measured before and after the 144 hour test period and the greater the difference in viscosity the greater the oxidative deterioration of the sulfurized calcium alkylphenolate composition. In addition, the test specimen is weighed before and after the test period and the greater the weight loss of test specimen the greater the corrosive deterioration of the test formulation. The larger the amount of copper, iron and lead moieties found in the oil after test, the greater the corrosive deterioration thereof.

The complexes of this invention are used in an amount ranging from 0.5 to 3 weight percent of the oil and the sulfurized calcium alkylphenolate ingredient in finished (dilute) lubricating oil compositions employed for engine use in desirably between about 0.1 and 7.5 weight percent with a calcium concentration of between about 0.06 and 0.5 weight percent, preferably about 0.1 and 0.4 weight percent. The concentrates can be formed for storage and transport and are subsequently blended to finished oil composition for engine use having a sulfurized calcium alkylphenolate of between about 0.1 and 10 weight percent.

In the finished lubricating oil compositions, other additives may be included such as supplementary dispersants, pour depressors, antioxidants, viscosity index improvers, oleagenous agents and antifoamant mixtures thereof. Exactly what other additives are included in the finished oil and the particular amounts therein will, of course, depend on the particular use the finished product is to be put to. One of the most suitable uses found for the overbased calcium alkylphenolate produced herein are lubricants for railway diesel engines.

A preferred class of dispersant additives is derivative of alkylene succinimide polyamides characterized by the formula:

$$R^2-CH-\overset{O}{\overset{\|}{C}}\diagdown_{N-CH_2CH_2(NHCH_2CH_2)_xNH_2}$$
$$CH_2-\underset{\|}{\underset{O}{C}}\diagup$$

where $R^2$ is alkenyl of from 50 to 200 carbons, x is an integer of from 0 to 10. Preferably, the alkylene group is polybutene having a molecular weight of about 1200 and the polyamine is tetraethylene pentamine.

A preferred antifoamant is a methyl silicone polymer (12500 cs at 770° F.) in kerosene.

A preferred pour depressant is a polymethacrylate.

The following examples further illustrate the invention but are not to be construed as limitations thereof.

EXAMPLE I

Preparation of polyoxypropylenediamine (molecular weight 360)-5-aminotriazole complex.

49.5 parts of the above amine (Jeffamine M-360) and 0.5 parts of 5-aminotriazole were mixed throughly for half hour at room temperature and the complex was isolated.

The complex above prepared can be generally represented as the following:

$$H_2NCH-CH_2[O-CH_2-\overset{CH_3}{\overset{|}{CH}}]_{2-3}NH_2\cdot NH_2-C\diagdown_{N-C-H}^{NH-N}$$

U.V. spectra confirmed the above structure as follows:
UV Analysis of Aminotriazole-Jeffamine M-360 Complex:
Complex: Max. abs. 2.67 at 194 nm
ATZ: Max. abs. 2.82 at 210 nm
Jeffamine M-360: Max. abs. 2.61 at 210 nm In the table below and in the tables following the other examples showing the medium speed diesel engine performance of formulations with and without the present additive, the constituents are identified by the following letters: A is a solvent neutral oil having an API gravity about 31, B is a solvent neutral oil having an API gravity of 26.5–29.0, C is a pale oil having an API gravity of 19 to 22, D is a 1 to 1 calcium carbonate overbased sulfurized calcium alkylphenolate, E is an alkenyl succinimide triethylene pentamine, F is a chlorinated n-paraffin containing 60% of chlorine, G is a methacrylate polymer, H is a blend of silicone and crystallite.

The above complex was tested in the UPOT test in formulation B below and reduced the corrosion value of a 10 TBN oil from 280 to 38 mg.

Medium Speed Diesel Engine Performance

|  | (A) | (B) |
|---|---|---|
| Composition, Wt. % |  |  |
| A | 5.00 | 5.00 |
| B | 48.30 | 46.30 |
| C | 37.00 | 37.00 |
| D | 5.55 | 5.55 |
| E | 4.05 | 4.05 |
| F | 0.05 | 0.05 |
| G | 0.05 | 0.05 |
| H | 150 | 150 |
| Experimental Additive of Ex. 1 | — | 2.00 |
| Union Pacific Oxidation Test |  |  |
| Weight Loss, mg. | 280 | 38 |
| Viscosity Increase, % | 160 | 51 |

EXAMPLE II

Preparation of "Jeffamine D230"-5-aminotriazole complex.

49.5 parts of the above amine which has a molecular weight of 230 and 0.5 parts of 5-aminotriazole were stirred thoroughly for ½ hr. at room temperature and product was isolated.

A typical 10 TBN medium speed diesel lubricant (A) gave a corrosion value of 280 mg in the UPOT test which was reduced in (B) by the addition of 2% of the additive.

Medium Speed Diesel Engine Performance

|  | (A) | (B) |
|---|---|---|
|  | 8847.00 | 8848.20 |
| Composition, Wt. % |  |  |

|   | (A) 8847.00 | (B) 8848.20 |
|---|---|---|
| A | 5.00 | 5.00 |
| B | 48.30 | 46.30 |
| C | 37.00 | 37.00 |
| D | 5.55 | 5.55 |
| E | 4.05 | 4.05 |
| F | 0.05 | 0.05 |
| G | 0.05 | 0.05 |
| H | 150 | 150 |
| Additive of Ex. 2 | — | 2.00 |
| Union Pacific Oxidation Test |  |  |
| Weight Loss, mg. | 280 | 81 |

The product can be generally represented as the following:

$$NH_2-CH-CH-[OCH_2-CH]_{2-3}-NH_2 \cdot NH_2-C\underset{N-C-H}{\overset{N-N}{\underset{|}{\overset{|}{\diagdown}}}}$$

with CH₃ groups.

The product was characterized by ultraviolet spectra as follows:

U.V. Analysis of Jeffamine D-230-Aminotriazole+ -
Max. abs. 2.63 at 199 nm

Jeffamine D-230: Max. abs. 2.85 at 213 nm Max. abs. 2.82 at 210 nm for 5-aminotriazole The existance of the complex is proved by the shift in the U.V. spectra.

EXAMPLE III

Preparation of "Jeffamine D230" benzotriazole complex.

49.5 parts of "Jeffamine D230" having a molecular of 230 was mixed with thorough stirring with 0.5 parts of benzotriazole at room temperature for ½ hr. The complex was isolated and tested as shown below. It reduced the corrosion value from 280 to 152.

Medium Speed Diesel Engine Performance

|  | (A) | (B) |
|---|---|---|
| Composition, Wt. % |  |  |
| A | 5.00 | 5.00 |
| B | 48.30 | 46.30 |
| C | 37.00 | 37.00 |
| D | 5.55 | 5.55 |
| E | 4.05 | 4.05 |
| F | 0.05 | 0.05 |
| G | 0.05 | 0.05 |
| H | 150 | 150 |
| Ex. 3 Complex | — | 2.00 |
| Union Pacific Oxidation Test |  |  |
| Weight Loss, mg. | 280 | 152 |

The complex was verified by U.V. It can be generally represented by the following:

$$H_2N-CH-CH_2-[O-CH_2CH]_{2-3}-NH_2 \cdot \text{(benzotriazole)}$$

with CH₃ groups.

U.V. Analysis of Jeffamine D-230-Benzotriole Complex=Max. abs. 2.85 at 206 nm 2nd Max. abs. 0.99 at 273 nm Benzotriole: Max. abs. 2.38 at 200 nm 2nd Max. abs. 0.80 at 259 nm Jeffamine D-230: Max. abs. 2.85 at 213 nm

EXAMPLE IV

Preparation of "Jeffamine BUD-2000"-benzotriazole complex.

49.5 parts of "Jeffamine BUD-2000" and 0.5 parts of benzotriazole were stirred thoroughly for ½ hr. at room temperature and the product was isolated.

As verified by U.V. analysis the complex had the formula:

$$H_2N-\overset{O}{\underset{}{C}}-NH-CH-CH_2-[O-CH_2-CH]-NH-\overset{O}{\underset{}{C}}-NH_2 \cdot \text{(benzotriazole)}$$

with CH₃ groups.

It showed maximum absorption of 2.73 at 210 nm and a second maximum of 1.25 at 254 nm. The Jeffamine BUD 2000 had a max. abs. of 2.15 at 210 nm (MCOH)

Benzotriazole showed: max. abs. 2.39 at 203 nm, 1.68 at 253 nm, 1.35 at 275 nm.

Medium Speed Diesel Engine Performance

|  | (A) | (B) |
|---|---|---|
| Composition, Wt. % |  |  |
| A | 5.00 | 5.00 |
| B | 48.30 | 46.30 |
| C | 37.00 | 37.00 |
| D | 5.55 | 5.55 |
| E | 4.05 | 4.05 |
| F | 0.05 | 0.05 |
| G | 0.05 | 0.05 |
| H | 150 | 150 |
| Jeffamine BUD-2000-Benzotriazole complex | — | 2.00 |
| Union Pacific Oxidation Test |  |  |
| Weight Loss, mg. | 280 | 152 |
| Viscosity Increase, % | 160 | 93 |

As shown in the above table, addition of 2 percent by weight of the complex reduced the corrosion value by 280 mg to 152 mg and reduced the viscosity increase to 93%.

The above and other exemplary complexes according to this invention are depicted in tabular form in Table 1 below reference being had to the generic formula given above:

| Example No. | Z | A | B | r | n |
|---|---|---|---|---|---|
| I | 2-aminoethyl | 5-amino | NH₂ | 1 | 2-3 |

-continued

| Example No. | Z | A | B | r | n |
|---|---|---|---|---|---|
| II | 2-aminopropyl | triazole | NH$_2$ | 1 | 2-3 |
| III | 2-aminopropyl | benzotriazole | NH$_2$ | 2-3 | 2-3 |
| IV | 2-ureidopropyl | benzotriazole | 2-ureido-propyl | 1 | 1 |
| V | aminomethyl | benzotriazole | NH$_2$ | 1 | 10 |
| VI | 3-aminobutyl | benzotriazole | NH$_2$ | 1 | 12 |
| VII | 1-ureidoethyl | benzotriazole | NH$_2$ | 1 | 12 |

The present invention may be embodied in other specific forms without departing from the spirit or essential attributes thereof and, accordingly, reference should be made to the appended claims rather than to the foregoing specification as indicating the scope of the invention.

We claim:

1. Polyoxyalkylene polyamine complexes of the formula:

$$Z-[(OCH_2CH)_n-B]_r \cdot A$$
$$\phantom{Z-[(OCH_2CH)_n}|$$
$$\phantom{Z-[(OCH_2CH)_n}Y$$

wherein A is 5-aminotriazole or benzotriazole; Y is hydrogen, or a lower alkyl group having 1 to 5 carbon atoms; Z is a hydrocarbon radical having 2-10 carbon atoms forming from 1 to 4 external ether linkages; n is 1 to 15 and r is 1 to 4; B is NH$_2$ or ureido except that when Z is ureidoalkyl and B is ureido, r can only be 1.

2. The complexes of claim 1 having the formula:

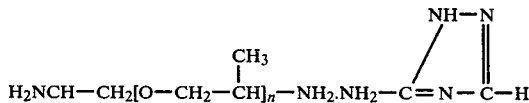

wherein n is 2 to 3.

3. The complexes of claim 1, having the formula:

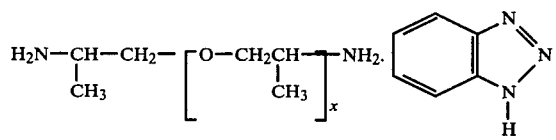

wherein n is 2 to 3.

4. The complexes of claim 1 having the formula:

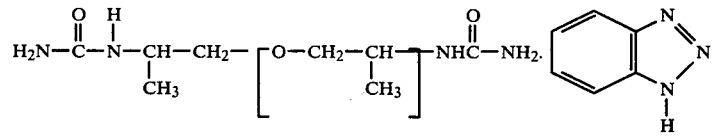

wherein x is 2 or 3.

5. The complexes of claim 1 having the formula:

$$H_2N-\overset{O}{\underset{}{C}}-\overset{H}{\underset{}{N}}-\overset{}{\underset{CH_3}{CH}}-CH_2-[O-CH_2-\overset{}{\underset{CH_3}{CH}}]-NH\overset{O}{\underset{}{C}}-NH_2 \cdot \text{(benzotriazole)}$$

6. A fully formulated medium speed diesel lubricant having a TBN of at least 5 and containing from 0.5 to 3 weight percent of a complex of claim 1 and 2% to 10% of a 1/1 calcium carbonate overbased sulfurized calcium alkylphenolate or 2/1 overbased sulfurized calcium alkylphenolate containing calcium sulfonate.

* * * * *